(12) United States Patent
Enomoto et al.

(10) Patent No.: US 7,012,678 B2
(45) Date of Patent: Mar. 14, 2006

(54) INSPECTION METHOD AND INSPECTION APPARATUS FOR DETECTING DEFECTS

(75) Inventors: Akio Enomoto, Chita-gun (JP); Kouichi Miyashita, Ama-gun (JP)

(73) Assignee: NGK Insulators, Ltd., Nagoya (JP)

( * ) Notice: Subject to any disclaimer, the term of this patent is extended or adjusted under 35 U.S.C. 154(b) by 328 days.

(21) Appl. No.: 10/258,961

(22) PCT Filed: Feb. 12, 2002

(86) PCT No.: PCT/JP02/01120

§ 371 (c)(1),
(2), (4) Date: Oct. 30, 2002

(87) PCT Pub. No.: WO02/082035

PCT Pub. Date: Oct. 17, 2002

(65) Prior Publication Data

US 2003/0112437 A1    Jun. 19, 2003

(30) Foreign Application Priority Data

Mar. 30, 2001  (JP) .............................. 2001-101182
Jan. 28, 2002  (JP) .............................. 2002-18474

(51) Int. Cl.
    *G01N 21/00*     (2006.01)
(52) U.S. Cl. ..................... 356/237.1; 356/337; 73/40.7
(58) Field of Classification Search ............. 356/237.1, 356/336–338, 343, 441; 250/574, 492.1; 73/40, 40.5 R, 40.7, 37, 38
See application file for complete search history.

(56) References Cited

U.S. PATENT DOCUMENTS 5,411,682 A        5/1995   Nagashima
5,640,236 A  *     6/1997   Nagashima ............. 356/237.1

FOREIGN PATENT DOCUMENTS

| JP | A 4-104038   | 4/1992 |
|----|--------------|--------|
| JP | A 6-134268   | 5/1994 |
| JP | A 7-174660   | 7/1995 |
| JP | A-2000-193582 | 7/2000 |

* cited by examiner

*Primary Examiner*—Michael P. Stafira
*Assistant Examiner*—Juan D Valentin, II
(74) *Attorney, Agent, or Firm*—Oliff & Berridge, PLC

(57) ABSTRACT

An inspection method for detecting a defect in a test object. A particulate is generated, then the generated particulate is introduced into a test object. Subsequently, light having high directivity is emitted such that the light passes in the vicinity of the test object to irradiate the particulate discharged from the test object, thereby making the particulate visible. An inspection apparatus for detecting a defect in a test object, including a particulate generator, a particulate introducing device which introduces the particulate into a test object, and a high directional light emitter emitting light passing in the vicinity of the test object and irradiating the particulate discharged from the test object to visualize the particulate. The inspection method and apparatus can detect a defect with high sensitivity and shorten an inspection time and a post-treatment time.

14 Claims, 8 Drawing Sheets

INSPECTION METHOD AND INSPECTION APPARATUS FOR DETECTING DEFECTS

TECHNICAL FIELD

The present invention relates to an inspection method and an inspection apparatus for detecting a defect of a test object and, more particularly, to an inspection method and an inspection apparatus for detecting a defect of a test object that allow a defect to be detected with high sensitivity and permit quick inspection and post-processing.

BACKGROUND ART

Test objects requiring inspection for detecting defects include, for example, porous members. Porous members are extensively used for filters or catalyst carriers, etc. Porous members are used, for instance, for the exhaust gas purifiers of heat engines, such as internal combustion engines, or combustion equipment, such as boilers, for reformers of liquid fuel or gas fuel, and for purifying facilities of water supply and sewerage. Furthermore, honeycomb-shaped porous members are used for diesel particulate filters or hot gas dust collectors to capture and remove particulate substances contained in a dust containing fluid, such as exhaust gas, emitted from a diesel engine.

A porous member used for such purposes mainly functions to capture and remove unwanted particulate substances when a fluid to be treated passes through micro-pores of the porous member, or to carry a catalyst on the surface and micro-pores of the porous member to bring the catalyst into contact with the fluid to be treated. In order to efficiently implement such functions, a porous member made of a thin film or wall is generally formed to have a shape, such as a tubular shape, a monolithic shape, or a honeycomb structural shape so as to increase the area that is brought into contact with a fluid to be treated. Therefore, the presence of a hole, i.e., a defect, that pierces the film or wall of a porous member interferes with the filtering performance of the porous member or the performance as a catalyst carrier. In the case of a nonporous member, a hole, that is, a defect, frequently prevents the performance expected of the material from being fully exhibited. The simplest method for inspecting such porous members or nonporous members for defects is visual inspection.

There are, however, some cases where the inspection is difficult, depending on the configuration, or the position or the size of a defect to be detected, of a test object, which may be a porous member or a nonporous member. For example, a honeycomb structure generally has numerous passages through the honeycomb structure in the axial direction (X direction), the passage is defined by partition walls, as shown in FIG. 8. In some cases, as shown in FIG. 2, the ends of the passages are alternately sealed, and the porous partitions capture and remove particulate substances. Hence, defects in the partitions of such a structure cannot be observed from outside.

There has been a known conventional method for inspecting a defect of such a test object, in which the upper end face of a honeycomb structure shown in, for example, FIG. 8 is covered with a white cloth, and soot-like substances generated by burning diesel fuel light oil is introduced from the lower end face of the honeycomb structure to cause the soot-like substances discharged from the upper end face to adhere to the white cloth, thereby obtaining the pattern shown in FIG. 7. This method for detecting a defect is called "the soot print method". In this case, the presence of a defect is indicated by a dark spot where more soot adheres. This method is handy and excellent in detecting the level of a defect and identifying the location of the defect. However, since the method involves the use of a soot-like substance, the soot-like substance that adheres to a honeycomb structure must be removed by heat treatment after inspection, and a few hours are required for such post-treatment. In addition, inspecting one test object requires 5 to 6 minutes.

There is another method in which a honeycomb structure is placed in water, and an air pressure is applied from one end face of the honeycomb structure to check for the presence of a defect from foaming on the other end face. The post-treatment of this method does not take as long as that of the aforesaid soot print method; however, the honeycomb structure has to be dried after the inspection, and also has to be de-foamed in water prior to the inspection, which takes time.

In making a porous member, there are some cases where a material is formed into a compact in a predetermined shape, then fired to produce pores thereby to turn the compact into the micro-porous member. Therefore, if it is possible to detect a defect already existing in the nonporous member prior to the firing process, it is economically advantageous because a defective member can be removed before it is fired.

In view of the above circumstances, an object of the present invention is to provide an inspection method and an inspection apparatus that may detect a defect with good sensitivity even if a test object has a shape that prevents a defect from being checked from outside or whether a test object is porous or nonporous.

Another object of the present invention is to provide an inspection method and an inspection apparatus that may identify a location of a defect easily.

Still another object of the present invention is to provide an inspection method and an inspection apparatus capable of recording a location of a defect easily.

A further object of the present invention is to provide an inspection method and an inspection apparatus with short inspection time and short or no pre-treatment and/or post-treatment time.

DISCLOSURE OF INVENTION

The present invention firstly provides an inspection method for detecting a defect, characterized in that a particulate is generated, the generated particulate is introduced into the test object, then light having high directivity is emitted such that the light passes in the vicinity of the test object to irradiate the particulate discharged from the test object, thereby making the particulate visible.

In the inspection method according to the present invention, to easily identify the location of a defect, it is preferable that the light is planarly emitted to detect a defect in a two-dimensional fashion. Furthermore, to easily record the location of detection, it is preferable that an image of the visualized and detected particulate is recorded by a camera. In addition, from the viewpoint of detection sensitivity and easier post-treatment, a particle diameter of the particulate generated is preferably 0.3 to 200 $\mu$m, and more preferably 0.5 to 50 $\mu$m, and still more preferably 1 to 10 $\mu$m. The inspection method for detecting a defect in accordance with the present invention can be preferably used when a test object is a porous member, and also preferably used when the test object is a honeycomb structure, especially a diesel particulate filter. In this case, from the aspect of detection sensitivity, the light is emitted such that it passes in the vicinity of a surface from which the particulate discharged and substantially in parallel to the surface from which the particulate is discharged.

The present invention secondly provides an inspection apparatus for detecting a defect, characterized by comprising: a particulate generating means for generating a particulate; a particulate introducing means for introducing the particulate generated by the particulate generating means into a test object; and a light emitting means for emitting light with high directivity that passes in the vicinity of the test object and irradiates the particulate discharged from the test object thereby to visualize the particulate.

To allow the location of detection to be easily identified, the light emitting means of the inspection apparatus for detecting a defect in accordance with the present invention is preferably a means for planarly emitting the light. Furthermore, to allow the location of a defect to be easily recorded, the inspection apparatus for detecting a defect in accordance with the present invention preferably further comprises a recording means for recording an image of the particulate that has been visualized and detected. In addition, from the viewpoint of detection sensitivity and easier posttreatment, the particulate generating means of the apparatus for detecting a defect in accordance with the present invention is preferably a means for generating particulates having particle diameters of 0.3 to 200 $\mu$m, more preferably 0.5 to 50 $\mu$m, and still more preferably 1 to 10 $\mu$m. The inspection apparatus for detecting a defect in accordance with the present invention is used for preferably a porous member, more preferably a honeycomb structure, and particularly a diesel particulate filter as a test object. In this case, from the aspect of detection sensitivity, the inspection apparatus for detecting a defect in accordance with the present invention preferably comprises the light emitting means for emitting light such that it passes substantially in parallel to a particulate discharge surface of the honeycomb structure from which the particulate is discharged.

BEST MODE FOR CARRYING OUT THE INVENTION

The present invention will be described in conjunction with a preferred embodiment thereof; however, the present invention is not limited to the following embodiment.

An important characteristic of the inspection method in accordance with the present invention is to emit light with high directivity, to irradiate the particulates that are discharged through a defective portion of a test object, so as to visualize and detect the particulates. Irradiating particulates with the light permits detection of a defect with high sensitivity even if a test object has a shape that does not allow a defect to be checked from outside.

The principle of the present invention will be explained in detail by taking, as an example, the detection of a defect of a honeycomb structure shown in FIG. 2; however, the present invention can be applied to test objects of a variety of shapes or materials rather than being applied only to a honeycomb structure.

Figure 2:
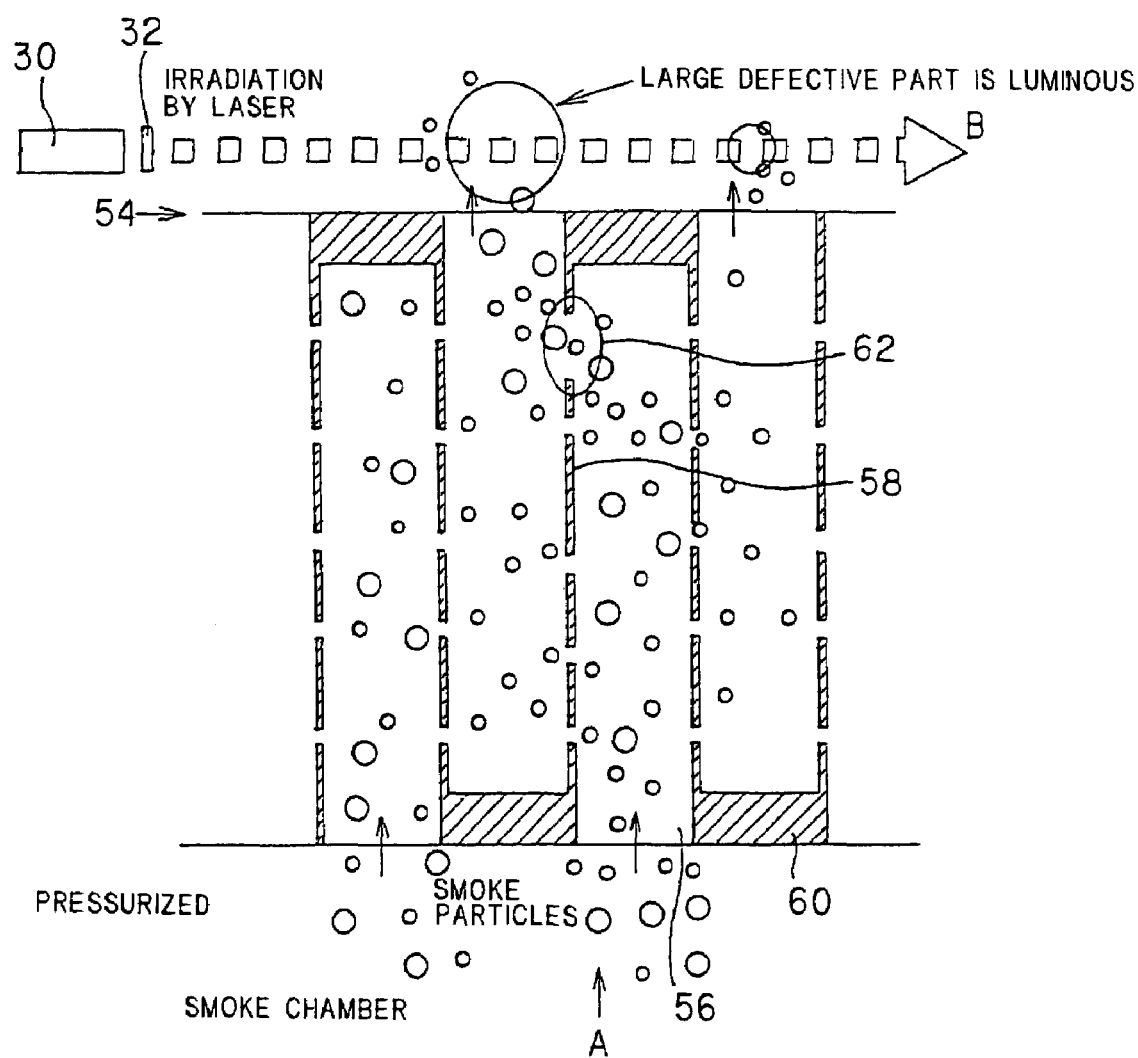
FIG. 2 is a schematic diagram showing a principle of the present invention.

If the honeycomb structure shown in FIG. 2 is a porous member, particulates are introduced from a direction A into a passage 56 where a partition 58 has a defect 62. The introduced particulates pass through the defect 62 and are discharged from a particulate discharge surface 54. If light with high directivity passes in a direction B in the vicinity of the particulate discharge surface 54, then the discharged particulates irregularly reflect the light, making them visible. In this case, if a passage has a larger defect, then it allows larger and more particulates to be discharged through the passage and larger particulates irregularly reflect more light. Hence, a spot having a larger defect irregularly reflects more light, thus making it possible to detect a passage that has a defect. If a sealing portion 60 has a defect, then particulates having larger particle diameters or more particulates are discharged through the passages affected by the defect, so that the passage having the defective sealing portion can be detected also. If the test object is nonporous, e.g., if the honeycomb structure shown in FIG. 2 is a compact prior to firing, then the introduced particulates are discharged only through a passage that has a defect in the partition 58 or the sealing portion 60. The discharged particulates irregularly reflect light, making themselves visible. This makes it possible to detect a defective passage.

To prevent the sensitivity from decreasing by the diffusion of discharged particulates, the light preferably passes in a range up to 5 mm from right above the particulate discharge surface, and more preferably up to 3 mm from right above the discharge surface. The light is preferably produced to planarly pass. To planarly produce the light, it is preferred to install a lens 32 in front of a light emitter 30 to planarly diffuse the light. The light can be planarly emitted also by scanning the light emitter 30. There are no particular restrictions on light as long as the light has high directivity, and has a wavelength irregularly reflected by the particulates used in the present method. However, laser beams are preferred, and a solid laser, a gas laser, a semiconductor laser, a dye laser, an excimer laser, a free electron laser, etc. may be preferably used. There are no particular restrictions on the wavelength of the light. For example, a red laser beam of about 650 nm, a green laser beam of about 532 nm, a purple laser beam of about 400 nm, etc. may be preferably used.

Figure 3:
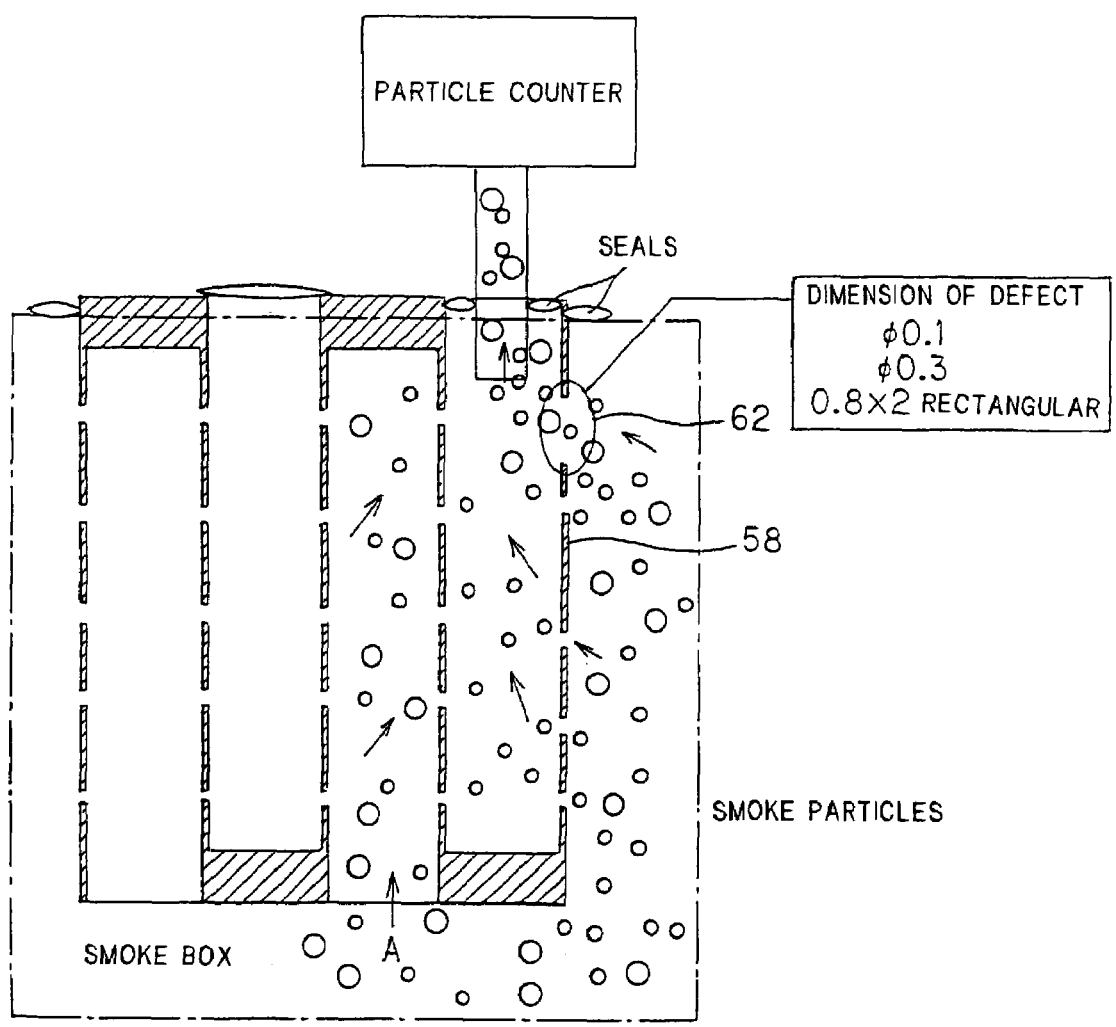
FIG. 3 is a schematic diagram showing an apparatus for checking the relationship between the types of defects and the particle size distribution of discharged particulates.
Figure 4:
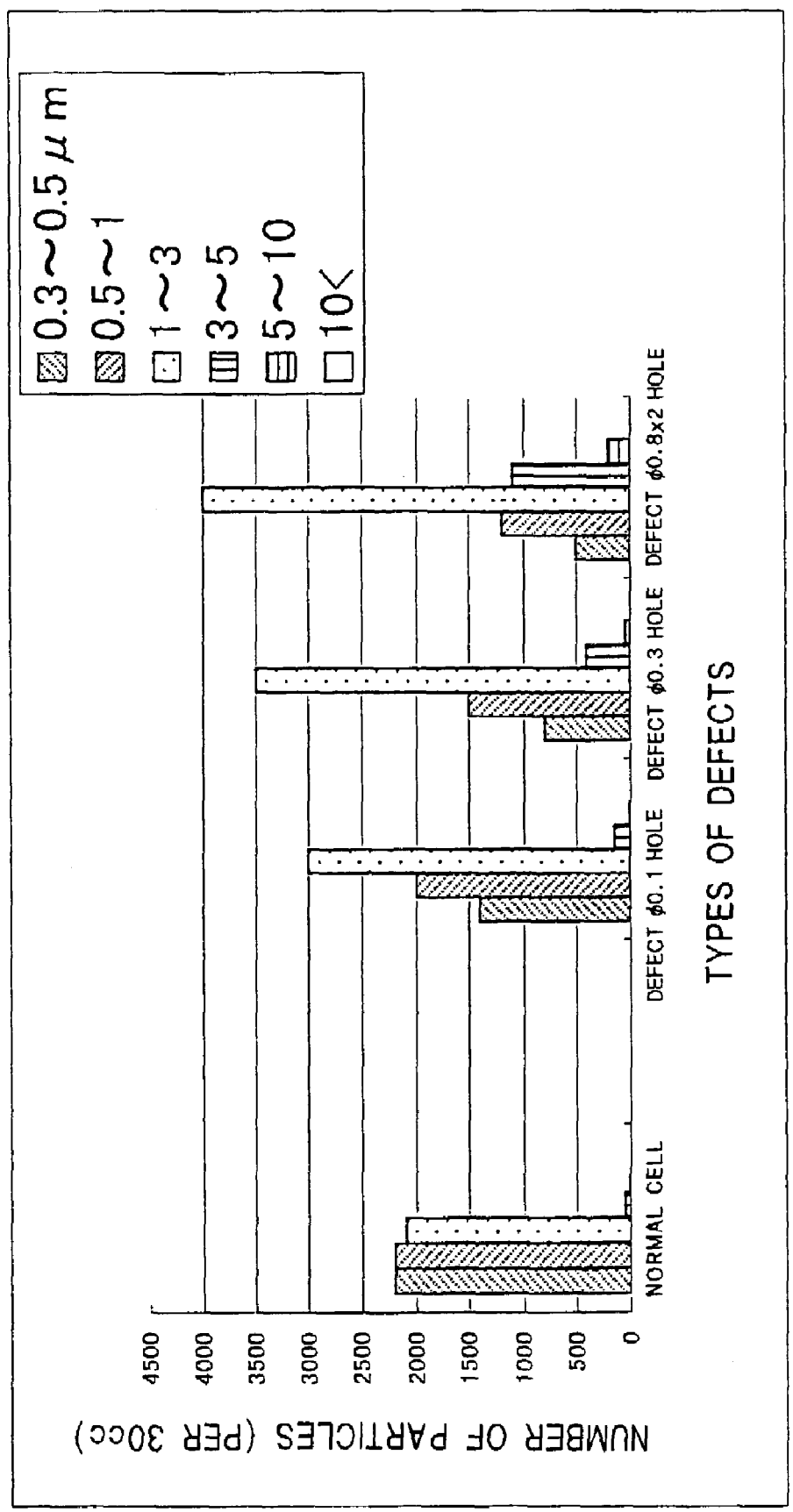
FIG. 4 is a graph showing an example of the results obtained by using the apparatus shown in FIG. 3.

The entire composition of the detection method in accordance with the present invention will now be explained. First, particulates are produced. There are no particular restrictions on the method for generating the particulates. Available methods include, for example, a method for burning incenses, such as an incense stick, a method for generating particulates of a glycol or the like and/or water by spraying them, a method for generating water particulates by a solid carbon dioxide, liquid nitrogen, a sprayer, a ultrasonic humidifier, a method using a commercial standard particle generator, and a method for raising dust of particulate powder of calcium carbonate or the like by a rocking apparatus or a blower. The particle diameter of the particulates generated by a particulate generating means may be appropriately selected by the shape of a test object to be inspected, or by a pore diameter if a test object is porous. For instance, as shown in the embodiment to be described hereinafter, a proper particle diameter that is suited to an object to be inspected can be selected by checking the relationship between the type of defect and the particle size distribution of particulates to be discharged (refer to FIG. 3 and FIG. 4). In the case of a porous test object, if the particle diameter is too large, then too many particulates will be captured in the pores of the porous test object, requiring post-treatment to be carried out to remove them. If the particle diameter is too small, then there will be little difference between the quantity of particulates discharged in the presence of defects and the quantity of particulates discharged in the absence of defects, as shown in FIG. 4. Particle diameters are, as mentioned previously, preferably in the range of 0.3 to 200 $\mu$m, more preferably in the range of 0.5 to 50 $\mu$m, and even more preferably in the range of 1 to 10 $\mu$m. However, even if generated particulates include particulates having particle diameters in a range other than the aforesaid ranges, they will still be in a preferred range as long as the quantity thereof included is at a level that allows the objective of the present invention to be fulfilled. Desirable particulates to be generated are those whose particle diameters do not change over time.

Subsequently, the generated particulates are introduced into a test object to be inspected. There are no particular restrictions on the introducing method; however, preferred methods include, for example, a method for storing generated particulates in a particle chamber until a predetermined concentration is reached, then a predetermined pressure is applied to lead the particulates into a test object, or a method in which a duct is provided at the top of a test object and a fan or the like is used for exhaust so as to guide particulates from a particle chamber into a test object. There are no particular restrictions on the concentration of particulates introduced into a test object. An appropriate concentration of a level may be selected, which allows detection to be effected by light with high directivity, such as a laser beam, and which ensures a clear contrast between a defective portion and the other than the defective portion. There are no particular restrictions on the applied pressure, and an appropriate pressure may be selected according to the type, the shape, or the like of a test object. As the number of defects increases, a lower pressure is enough to detect a defect, because the pressure loss in the test object decreases as the size of a defect increases. As the number of defects decreases or as the size of a defect decreases, the pressure loss in a test object increases, requiring a higher pressure to be applied. Furthermore, as the pressure applied is increased, the distance, such that the particulates discharged from a test object move in a laminar flow, increases. Therefore, the defect gets to be detected even if light is passed away from a test object. This is, however, undesirable for a porous test object because if the pressure applied is too high, then many particulates flow out, passing through the porous test object. This is disadvantageous cost-wise in that, for example, more particulates are required, and collecting them is more difficult.

The test object to be inspected has no particular restrictions on the shape, material, the pore diameter in the case of a porous member, applications, etc. as long as they may incur defects. The present invention can be applied to test objects of any shapes, materials, the pore diameters in the case of porous members, applications, etc. If, for example, a test object is porous, then a fluid to be treated is preferably discharged from a surface portion, especially preferably from a planar portion. Whether the test object is porous or nonporous, the test object is preferably such that particulates are discharged from a surface portion and preferably discharged from a planar portion. Since the present invention can be applied also to a porous test object, it is desirable that a test object is porous. It is also desirable that the test object has, for example, a honeycomb structure, which is difficult to directly detect a defect from outside, and the test object is further preferably used especially with a diesel particulate filter or a hot gas dust collector or the like. It is also desirable to use, as a test object, a nonporous member that turns into a porous member by firing, e.g., a honeycomb structure after formed and before fired, because a defect can be discovered before firing. In such a case, the structure is preferably used as a test object after forming it into a predetermined shape and drying it to maintain the shape.

Subsequently, as mentioned above, light is emitted such that the light with high directivity passes in the vicinity of a test object to be inspected, and a defect can be detected by observing the image obtained from the irregular reflection of the light against the particulates discharged from the test object. A camera, an optical video camera, a CCD camera, etc. can be preferably used to record the visualized image.

The inspection apparatus in accordance with the present invention will now be explained in conjunction with FIG. 1.

Figure 1:
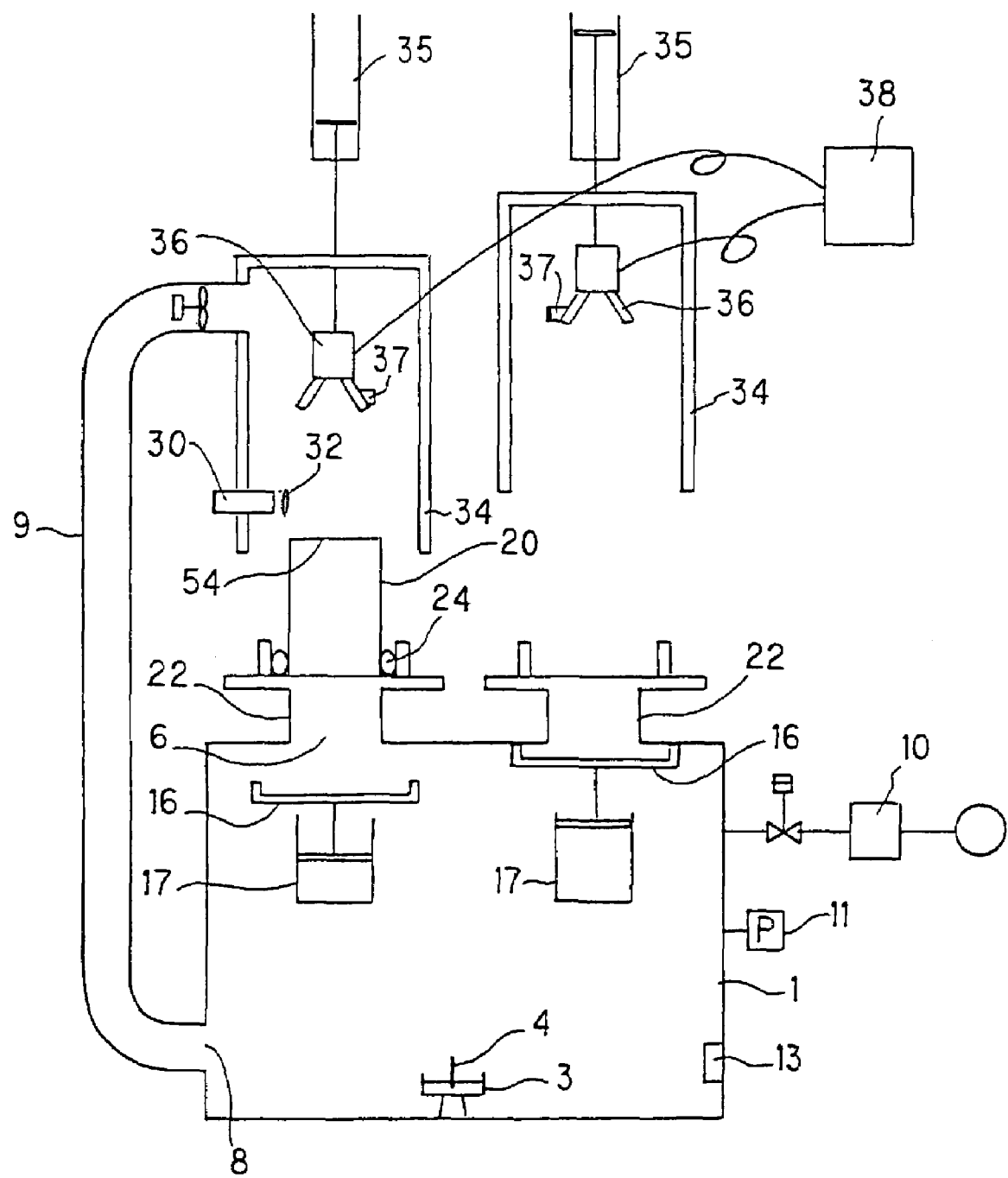
FIG. 1 is a schematic diagram showing a preferred apparatus in accordance with the present invention.

FIG. 1 shows a preferred embodiment of the inspection apparatus in accordance with the present invention. In FIG. 1, the inspection apparatus according to the present invention is equipped with a particle chamber 1, two mounting bases 22, two laser beam emitters as a light emitter 30 each, two hoods 34, and two CCD cameras 36. The configuration shown in FIG. 1 is adapted to inspect two test objects; however, the inspection apparatus according to the present invention may have a single test object or three or more test objects.

In the particle chamber 1, an incense stick 4 serving as a particulate generating means is set on an incense stick stand 3, and incense stick smoke is generated by burning the incense stick 4. The incense stick smoke is composed of particulates having particle diameters in the range of about 0.3 to about 10 $\mu$m. There are no particular restrictions on the particulate generating means in the present invention. Particulate generating means that may be used includes an apparatus for burning incenses, such as the aforesaid incense stick, an apparatus for generating particulates of glycols and/or water by spraying them, an apparatus for generating water particulates by a solid carbon dioxide, liquid nitrogen, a sprayer, a ultrasonic humidifier, or the like, an apparatus using a commercial standard particulate generator, and an apparatus for raising dust of particulate powder of calcium carbonate or the like by a vibrating apparatus, blower, or the like. The particulate generating means does not have to be in the particle chamber 1. The particulate generating means may alternatively be provided outside the particle chamber, and generated particulates may be led into the particle chamber 1.

A particulate inlet 6 through which particulates are introduced from the particle chamber 1 into a test object 20 is provided at an upper part of the particle chamber 1. A pressurizing mechanism 10 serving as a particulate introducing means is provided. The interior of the particle chamber 1 is pressurized by the pressurizing mechanism 10, and the particulates in the particle chamber 1 pass through the particulate inlet 6 into the test object 20 to be inspected.

To maintain the pressure in the particle chamber 1 at a constant level, a compressor equipped with a regulator or the like, is preferably used as the pressurizing mechanism 10. The pressurizing force is preferably in the range of 1 to 30 Pa for a porous test object, while it is preferably in the range of 100 to 20000 Pa for a nonporous test object. Preferably, therefore, the pressurizing mechanism is able to apply pressurizing forces in the above ranges.

A pressure gauge 11 and a particulate concentration meter 13 are installed in the particle chamber 1 to permit the control of pressure and particulate concentration in the particle chamber 1. Furthermore, a particulate circulation port 8 and a particulate circulation pipe 9 are provided to return discharged particulates back into the particle chamber 1. The apparatus in accordance with the present invention shown in FIG. 1 is configured so as to allow two test objects 20 to be inspected, and the two particulate inlets 6 are provided with particulate inlet covers 16 coupled to cylinders 17 so that the particulate inlets 6 may be opened and closed by the cylinders 17 moving up and down. As the cylinders 17 move up and down, the particulate inlets 6 can be opened and closed, and the particulate inlets 6 can be closed when not in use.

At the tops of the particulate inlets 6, the mounting bases 22 that have openings connected to the particulate inlets 6 are provided so as to allow the test objects 20 to be detachably mounted thereon. The test object 20 is set on the mounting base 22, with its outer periphery sealed by a seal 24. The seal 24 may take diverse shapes according to the shape of the test object 20 to be inspected. Since the mounting bases 22 are thus configured, all particulates passing through the particulate inlets 6 are guided into the test objects 20.

Hoods 34 coupled to the cylinders 35 so as to permit their own upward and downward movement are provided above the test objects 20. When inspection is performed, the hoods 34 move down to prevent a disturbance, such as wind, which disturbs the flow of the particulates discharged from the test objects 20.

A laser beam emitter serving as the light emitter 30 is provided above the test object 20. The laser beam emitter, which is a light emitting means with high directivity, is preferably provided to permit upward and downward movement, and to preferably allow a light beam to pass in the range up to 5 mm from right above the discharge surface and further preferably in the range up to 3 mm from right above the discharge surface during inspection. A lens 32 is provided in front of the light emitter 30 to diffuse light so that the light planarly passes in parallel to the particulate discharge surface 54 of the test object 20. In FIG. 1, a He—Ne laser beam emitter is installed as the light emitter. There are no particular restrictions on the light emitting means according to the present invention, as long as it emits light that has a wavelength ensuring irregular reflection off the particulates produced by the particulate generating means in the method and that has high directivity. A laser beam is preferred. Preferably, a light emitting means such as, for example, a solid laser, a gas laser, a semiconductor laser, a dye laser, an excimer laser, a free electron laser, etc. is provided. The light beams emitted by such a light emitting means include, for example, red laser beams of about 650 nm, green laser beams of about 532 nm, and purple laser beams of about 400 nm.

Further above the test objects 20, CCD cameras 36 connected to a monitor 38 are installed as the recording means, vertically facing downward, so as to be able to photograph and record irregularly reflected laser beams. As the recording means, cameras, optical video cameras, or the like may be also used in place of the CCD cameras. Right under the lenses of the CCD cameras 36, air purging mechanisms 37 are provided that are capable of applying positive pressure to prevent particulates from adhering to the camera lenses.

The present invention will now be explained in further detail in conjunction with following examples; however, the present invention should not be deemed to be limited to the examples. In the following tests, cylindrical porous honeycomb structures (hereinafter referred to simply as "filters"), which have a diameter of 150 mm, a length of 150 mm, and a cell density of 40 cells/cm$^2$ and which are used as diesel particulate filters, have been used as assessment test objects. For the examples and comparative examples, the filters (a), (b), and (c) have been used. (Relationship between the types of defects and the particle size distribution of discharged particulates)

A filter having a passage (cell) with a circular defect of 0.1-mm in diameter, a filter having a passage (cell) with a circular defect of 0.3-mm in diameter, a filter having a passage (cell) with a rectangular defect of 0.8 mm×2 mm, and a filter having no defective cell (normal cell) were prepared. By using the apparatus shown in FIG. 3, the particulates passing through the defective cells were sucked in by a particle counter and the particle size distribution of the sucked particulates was measured. FIG. 4 shows a measurement example of the relationship between the types of defects 62 and the particle size distribution of the particulates discharged to the particulate discharge surface 54 through the defective cells. The quantity of the particulates discharged through the defective cells was smaller than that of the particulates discharged through the normal cells in the range of 0.3 to 1 $\mu$m, while it was larger than that of the particulates discharged through the normal cell in the range of 1 to 10 $\mu$m characterized in that more irregularly reflected light is emitted. Hence, it has been found that particulates having particle diameters in the range of about 1 to about 10 $\mu$m are appropriate for detecting defects when the objects to be inspected are the above filters and the diameters of defects to be discovered are in the range of about 0.1 to about 0.8 mm.

EXAMPLE 1

Figure 5:
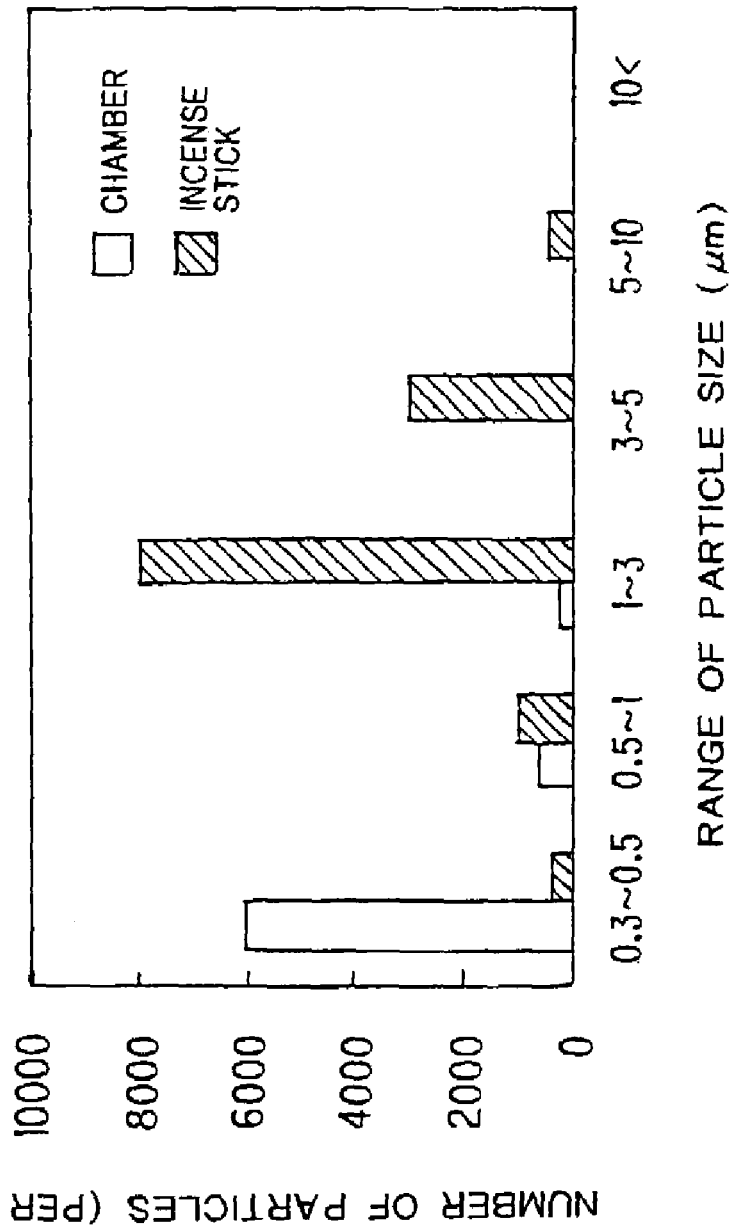
FIG. 5 is a graph showing the particle size distribution of particulates generated by burning an incense stick.
Figure 6A:
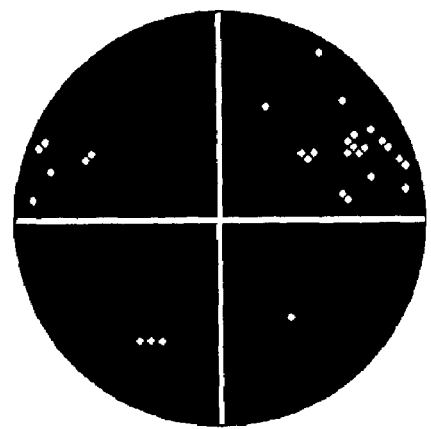
FIG. 6(a), (b), and (c) are diagrams showing the images of the locations of defects of a test object obtained in first through third embodiments.

Using the seal 24, the filter (a) was set on the mounting base 22 of the apparatus for checking a test object for defects shown in FIG. 1. Then, an incense stick was burnt to generate particulates of the particle size distribution shown in FIG. 5. When the concentration of the particulates reached 300 cells/cc, the inside of the particulate chamber was pressurized at 10 Pa by the pressurizing mechanism 10 to introduce the particulates into the filter (a). A He—Ne laser beam emitter was used as the light emitter 30, and a laser beam was emitted through the lens 32, the laser beam being planarly passed substantially in parallel to the upper surface of the filter (a) (the particulate discharge surface 54) at 3 mm above the filter (a). The laser beam irregularly reflected by discharged particulates was photographed by the CCD camera 36 and observed and recorded by the monitor 38. The time required from the start of the inspection to the photographing was five seconds. The filtering function remained intact even when post-treatment was not carried out after the inspection. The photographed image is shown in FIG. 6(a). In FIG. 6(a), the bright spots indicate the spots where more irregular reflection of the laser beam against the particulates took place. This means that numerous larger particulates were discharged through the spots, indicating the presence of defects at the spots.

EXAMPLES 2 AND 3

The inspections were carried out for the filters (b) and (c) in the same manner as that of Example 1. The time required from the start of the inspection to photographing was five seconds. The filtering functions remained intact even when post-treatment was not carried out after the inspection. The photographed images are shown in FIG. 6(b) and FIG. 6(c).

COMPARATIVE EXAMPLES 1–3

The filters (a) through (c) were subjected to an inspection based on the soot print method. The time required from the start of the inspection until a soot print. was completed was five minutes. After the inspection, a large volume of soot adhering to the insides of the filters had to be removed. It took about eight hours to remove the soot by heating and burning. The obtained soot print images are shown in FIG. 7(a), FIG. 7(b), and FIG. 7(c).

Figure 6B:
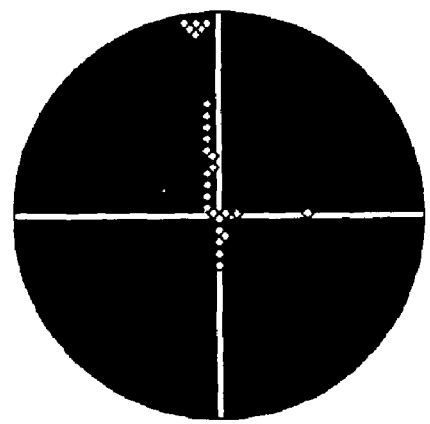
Figure 6C:
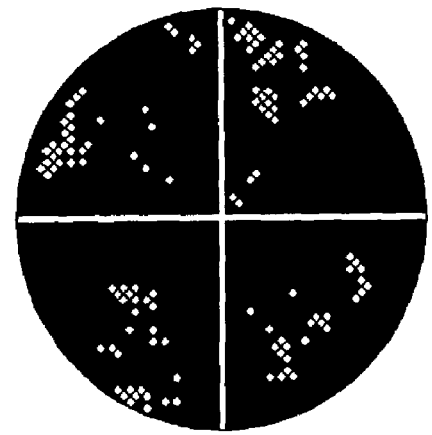
Figure 7A:
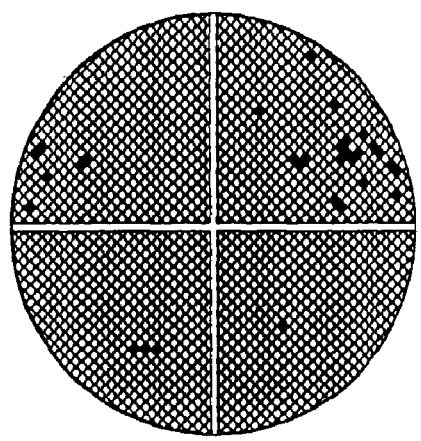
FIG. 7(a), (b), and (c) are diagrams showing the images of the locations of defects of a test object obtained in first through third comparative examples.
Figure 7B:
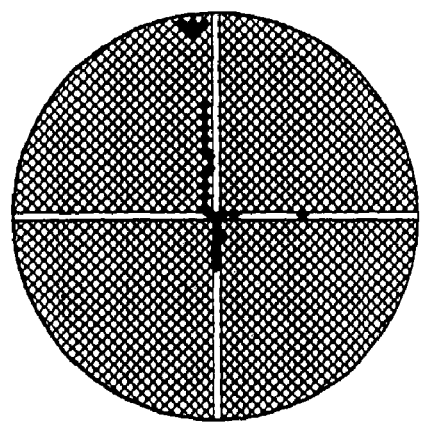
Figure 7C:
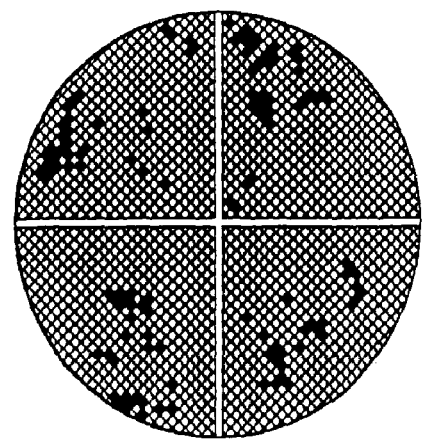
Figure 8:
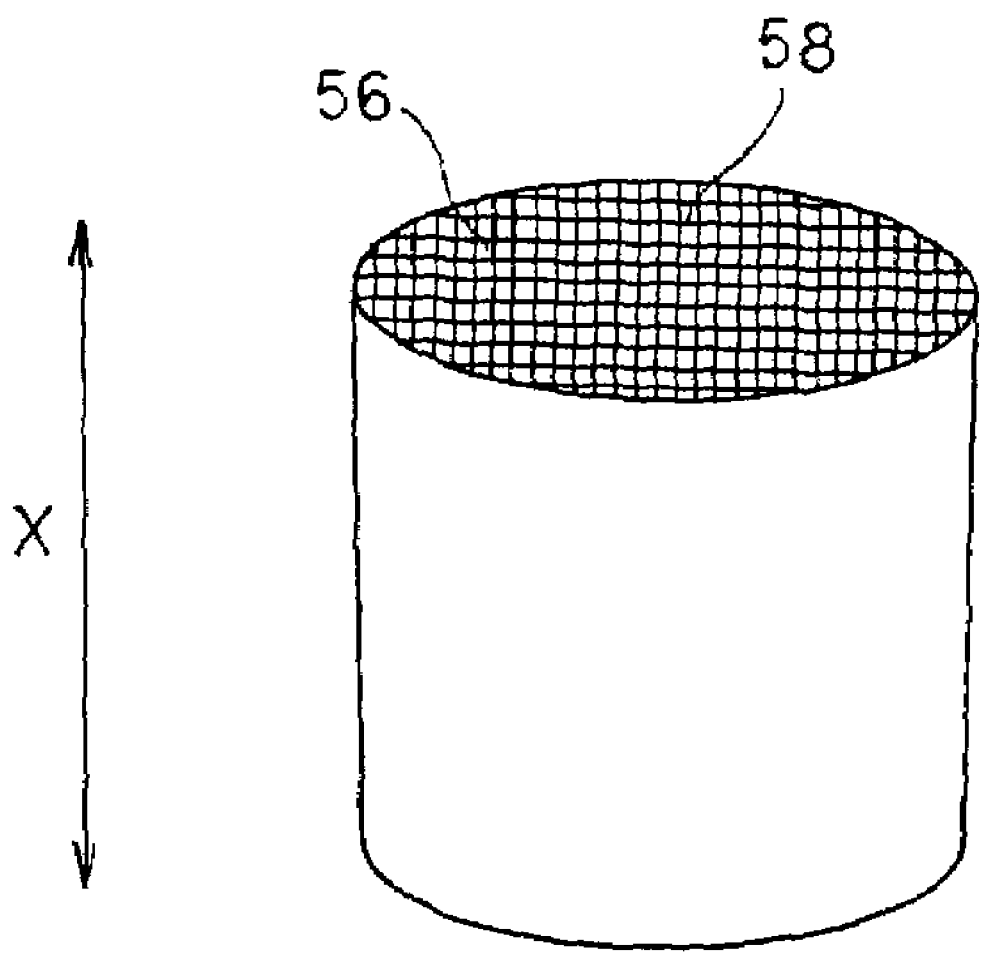
FIG. 8 is a perspective view showing an example of a honeycomb structure.

The comparison between FIG. 6(a) through (c) (the method in accordance with the present invention) and FIG. 7(a) through (c) (the conventional soot print method) indicated very good consistency, proving the reliability of the method in accordance with the present invention. The images obtained by the method according to the present invention exhibited higher contrast with respect to each cell, permitting the detection of the locations of the defects to be identified with higher sensitivity.

INDUSTRIAL APPLICABILITY

Using the method and apparatus in accordance with the present invention has made it possible to detect defects with high sensitivity even in a test object having a shape that does not allow defects to be checked from outside. Moreover, it has become easier to identify the locations of defects and to record the locations of defects. In addition, the inspection time and the time required for the pre-treatment and the post-treatment have been shortened, or the need for the pre-treatment and the post-treatment before and after an inspection has been obviated.

What is claimed is:

1. An inspection method for detecting a defect, the method comprising:
   a particulate is generated,
   the generated particulate is introduced into the test object, wherein the generated particulate is introduced by a pressurizing force that is applied so as to provide a differential pressure of 1 to 30 Pa between a particulate inlet and outlet, then
   light having high directivity is emitted such that the light passes in the vicinity of the test object to irradiate the particulate discharged from the test object, thereby making the particulate visible,
   wherein the test object is a porous honeycomb structure.

2. The inspection method for detecting a defect according to claim 1, characterized in that the light is planarly emitted to detect a defect in a two-dimensional fashion.

3. The inspection method for detecting a defect according to claim 2, characterized in that an image of the visualized and detected particulate is recorded by a camera.

4. The inspection method for detecting a defect according to claim 1, characterized in that a particle diameter of the particulate generated is 0.3 to 200 µm.

5. The inspection method for detecting a defect according to claim 1, characterized in that the honeycomb structure is a diesel particulate filter.

6. The inspection method for detecting a defect according to claim 1, characterized in that the light is emitted such that it passes in the vicinity of a surface from which the particulate is discharged and substantially in parallel to the surface from which the particulate is discharged.

7. An inspection apparatus for detecting a defect, characterized by comprising:
   a particulate generating means for generating a particulate;
   a particulate introducing means for introducing the particulate generated by the particulate generating means into a test object;
   a light emitting means for emitting light with high directivity that passes in the vicinity of the test object and irradiates the particulate discharged from the test object thereby to visualize the particulate,
   wherein the particulate introducing means applies a pressurizing force so as to provide a differential pressure of 1 to 30 Pa between a particulate inlet and outlet, and
   wherein the test object is a porous honeycomb structure.

8. The inspection apparatus for detecting a defect according to claim 7, characterized in that the light emitting means is a means for planarly emitting the light.

9. The inspection apparatus for detecting a defect according to claim 8, characterized by further comprising a recording means for recording an image of the particulate that has been visualized and detected.

10. The inspection apparatus for detecting a defect according to claim 7, characterized in that the particulate generating means is a means for generating particulates having particle diameters of 0.3 to 200 µm.

11. The inspection apparatus for detecting a defect according claim 7, characterized in that the honeycomb structure is a diesel particulate filter.

12. The inspection apparatus for detecting a defect according to claim 7, characterized by comprising the light emitting means for emitting light such that it passes substantially in parallel to a particulate discharge surface of the honeycomb structure from which the particulate is discharged.

13. An inspection apparatus for detecting a defect of a test object, characterized by comprising:
   a particulate generator generating a particulate;
   a particulate introducing device introducing the particulate into the test object; and
   a high directional light emitter emitting light passing in the vicinity of the test object and irradiating the particulate discharged from the test object thereby to visualize the particulate,
   wherein the particulate introducing device applies a pressurizing force so as to provide a differential pressure of 1 to 30 Pa between a particulate inlet and outlet, and
   wherein the test object is a porous honeycomb structure.

14. The inspection apparatus for detecting a defect according to claim 13, the particle generator is a generator generating particulates having particle diameters of 0.3 to 200 µm.

* * * * *